US008755865B2

(12) United States Patent
Gonzalez Molezzi et al.

(10) Patent No.: US 8,755,865 B2
(45) Date of Patent: Jun. 17, 2014

(54) SYSTEM AND METHOD TO ADAPTIVELY CONTROL CONTRAST-ENHANCED DIAGNOSTIC IMAGING PROCEDURE (75) Inventors: Marcela Gonzalez Molezzi, Wauwatosa, WI (US); Holly Ann McDaniel, Waukesha, WI (US); Scott Eugene Trevino, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 55 days.

(21) Appl. No.: 13/101,216

(22) Filed: May 5, 2011

(65) Prior Publication Data

US 2011/0208046 A1 Aug. 25, 2011

Related U.S. Application Data (63) Continuation of application No. 11/691,605, filed on Mar. 27, 2007, now Pat. No. 7,974,682.

(60) Provisional application No. 60/867,060, filed on Nov. 22, 2006.

(51) Int. Cl.
*A61B 6/00* (2006.01)
*A61B 5/00* (2006.01)
*A61B 5/055* (2006.01)
*A61B 8/08* (2006.01)
*A61B 6/03* (2006.01)
*A61B 8/00* (2006.01)

(52) U.S. Cl.
CPC .............. *A61B 6/481* (2013.01); *A61B 5/7285* (2013.01); *A61B 5/055* (2013.01); *A61B 8/481* (2013.01); *A61B 6/541* (2013.01); *A61B 6/03* (2013.01); *A61B 8/543* (2013.01)
USPC ............................ 600/431; 600/427; 600/428

(58) Field of Classification Search
None
See application file for complete search history.

(56) References Cited

U.S. PATENT DOCUMENTS

| 5,459,769 | A | * | 10/1995 | Brown | 378/4 |
| 5,687,208 | A | * | 11/1997 | Bae et al. | 378/8 |
| 5,840,026 | A | | 11/1998 | Uber, III et al. | |
| 6,188,744 | B1 | * | 2/2001 | Shinohara et al. | 378/8 |
| 6,236,706 | B1 | * | 5/2001 | Hsieh | 378/8 |
| 6,337,992 | B1 | * | 1/2002 | Gelman | 600/425 |

(Continued)

FOREIGN PATENT DOCUMENTS

JP 2003319934 A 11/2003

OTHER PUBLICATIONS

Office Action from corresponding Japanese Application No. JP 2007-296184, dated Sep. 4, 2012.

*Primary Examiner* — Long V. Le
*Assistant Examiner* — Angela M Hoffa
(74) *Attorney, Agent, or Firm* — Ziolkowski Patent Solutions Group, SC (57) ABSTRACT A system and method are provided for determining individualized scan and injection protocols for contrast-enhanced diagnostic imaging. Taking into account parameters specific to the scan subject, injection-related parameters, and scan parameters, the system and method can determine an optimal timing for a scan sequence to begin, to ensure that the scan sequence coincides with a desired contrast enhancement. Some embodiments further provide for real-time triggering of the scan commencement based on bolus tracking, and can adapt the scan and injection protocols in real-time based on monitored dynamic scan subject parameters and/or actual enhancement values determined from image data.

19 Claims, 5 Drawing Sheets

(56) References Cited

U.S. PATENT DOCUMENTS

| | | |
|---|---|---|
| 6,385,483 B1 | 5/2002 | Uber, III et al. |
| 6,397,097 B1 | 5/2002 | Requardt |
| 6,522,713 B1 * | 2/2003 | Valiga et al. ............... 378/4 |
| 6,763,082 B2 * | 7/2004 | Ozaki ............... 378/8 |
| 6,970,735 B2 | 11/2005 | Uber, III et al. |
| 7,974,682 B2 * | 7/2011 | Gonzalez Molezzi et al. ............... 600/432 |
| 8,150,125 B2 * | 4/2012 | Baumgart et al. ............ 382/130 |
| 8,208,699 B2 * | 6/2012 | Hay et al. ............... 382/128 |
| 2001/0056233 A1 | 12/2001 | Uber, III et al. |
| 2002/0068865 A1 * | 6/2002 | Meaney et al. ............... 600/415 |
| 2003/0050556 A1 | 3/2003 | Uber, III et al. |
| 2003/0092983 A1 | 5/2003 | Baker et al. |
| 2003/0095144 A1 * | 5/2003 | Trevino et al. ............... 345/764 |
| 2003/0158476 A1 | 8/2003 | Takabayashi et al. |
| 2004/0114706 A1 * | 6/2004 | Ikeda et al. ............... 378/4 |
| 2004/0162488 A1 | 8/2004 | Uber, III et al. |
| 2004/0181147 A1 | 9/2004 | Prince |
| 2005/0203389 A1 | 9/2005 | Williams |
| 2006/0030773 A1 | 2/2006 | Uber, III et al. |
| 2006/0241402 A1 | 10/2006 | Ichihara et al. |
| 2006/0264741 A1 | 11/2006 | Prince |
| 2008/0033289 A1 | 2/2008 | Haras |
| 2008/0097196 A1 | 4/2008 | Licato et al. |
| 2008/0097197 A1 | 4/2008 | Kalafut et al. |
| 2008/0253634 A1 | 10/2008 | Hay et al. |
| 2008/0300480 A1 | 12/2008 | Meaney et al. |
| 2008/0319309 A1 | 12/2008 | Bredno et al. |

* cited by examiner

SYSTEM AND METHOD TO ADAPTIVELY CONTROL CONTRAST-ENHANCED DIAGNOSTIC IMAGING PROCEDURE

CROSS-REFERENCE TO RELATED APPLICATION

The present application is a continuation of and claims the benefit of U.S. application Ser. No. 11/691,605, filed Mar. 27, 2007, which claims the benefit of U.S. provisional application Ser. No. 60/867,060, filed Nov. 22, 2006, the disclosures of which are incorporated herein by reference.

BACKGROUND OF THE INVENTION

The present invention is related generally to diagnostic imaging, and, more particularly, to a system and method for determining scan protocols for contrast enhanced diagnostic imaging scans. Embodiments of the invention take into account various static and dynamic scan subject parameters, as well as injection process parameters and scan parameters, to coordinate the delivery of a contrast agent with the commencement of a scan sequence such that the scan sequence will coincide with the peak contrast enhancement.

Contrast-enhancement through administration of a contrast agent is well known in multiple diagnostic imaging modalities, including computed tomography (CT), magnetic resonance (MR), x-ray, ultrasound, positron-emission tomography (PET), spectroscopy, and the like. By administering a contrast agent to a scan subject, an improvement in image quality and contrast can be achieved due to properties of the contrast agent. Types of useful contrast agents vary by imaging modality and the anatomy of interest. Two common types of contrast agents are barium, for x-ray based imaging, and gadolinium, for magnetic resonance based imaging.

The quality of many contrast-enhanced imaging procedures is substantially dependant upon the contrast agent, both in terms of image quality and scan parameters (such as radiation dosage). However, the contrast enhancement provided by a contrast agent varies according to a variety of factors influenced by the specific scan subject, the contrast injection process, and the type of scan. Since the goal of contrast-enhanced imaging is to acquire scan data while the contrast agent is providing the desired contrast enhancement, the timing of contrast agent administration with respect to the commencement of the scan sequence is important.

Typically, the procedure or protocol for a contrast-enhanced imaging scan is determined by a radiologist and technologist. No single approach for determining when and how to administer the contrast agent prior to scanning is effective in all cases. Some general timing guidelines exist for various scans and contrast agents, but an appreciable amount of guesswork is still involved. Factors which practitioners must consider include: the type of tissue to be imaged, the scan subject or patient's body size, heart rate, renal function, age, gender, and oxygen level in the blood, the injection concentration, volume, flow rate, flow pattern, duration, and use of saline, as well as the scan duration, radiation exposure, and presence and number of scan phases. Thus, an injection and scan protocol which may apply for a given scan subject may be inappropriate for a subsequent scan subject, even where the subsequent scan subject is having an identical scan and contrast administration. Further complicating the practitioner's task is the fact that, as scanner technologies advance, scan times shorten and fields of view narrow. Therefore, the timing protocol of a scan can be more complex and require more precision than a practitioner estimate can provide.

It would therefore be desirable to have a system and method capable of accounting for a wide variety of scan subject-specific, injection-specific, and/or scan-specific factors in determining a protocol for contrast agent injection and scanning. It would be further desirable for such system and method to automate the determination and/or execution of the protocol to the extent that such automation will improve image quality and scan subject throughput.

BRIEF DESCRIPTION OF THE INVENTION

The present invention provides a system and method for overcoming the aforementioned drawbacks. In particular, embodiments of the invention take into account scan subject parameters, injection process parameters, and scan parameters in order to coordinate contrast agent delivery with a scan sequence such that the scan sequence, or a desired portion thereof, will coincide with the a desired contrast enhancement.

Therefore, in accordance with one aspect of the invention, a system control for a diagnostic imaging apparatus is provided. The system control may include a user interface, a scan subject monitor, a scan protocol module, a contrast delivery device, and an acquisition control. The user interface is adapted to permit a user to enter data specific to a given scan and the scan subject monitor is configured to monitor at least one dynamic parameter of the scan subject. The scan protocol module is connected to receive the data entered on the user interface and the at least one dynamic scan subject parameter, and is programmed to prescribe a scan protocol to optimize contrast enhancement. In accordance with this prescribed scan protocol, the contrast delivery device is controlled by the scan protocol module to cause a contrast agent to be delivered to a scan subject. The acquisition control is configured to coordinate commencement of the given scan in accordance with the scan protocol In accordance with another aspect of the invention, the invention also provides for a method of contrast-enhanced diagnostic imaging. The method includes estimating, for a given scan subject, a post-delivery time at which a desired contrast agent enhancement value is reached. This estimation is performed based on a number of subject parameters, a number of contrast agent parameters, and a number of scan parameters. The method further includes administering the contrast agent and timing at least a portion of an imaging scan sequence to coincide with the post-delivery desired contrast enhancement time of the contrast agent. During the scan, at least one of the number of contrast agent parameters and the number of scan parameters is adapted, in order to maintain the timing of the desired contrast enhancement and the portion of the imaging scan sequence. An image is then reconstructed of the scan subject based at least on scan data acquired during the post-delivery desired contrast enhancement time.

In accordance with a further aspect of the invention, a computer readable storage medium has a set of instructions stored thereon which, when executed by a computer, causes the computer to prompt a user to enter patient-specific information for a given scan patient and to prompt the user to select a scan type. The computer is also caused to receive bolus tracking data for the given patient and provide an individualized scan protocol defining a contrast agent delivery and scan sequence timing, based upon the patient-specific information, the scan type, and the bolus tracking data.

Various other features and advantages of the present invention will be made apparent from the following detailed description and the drawings.

BRIEF DESCRIPTION OF THE DRAWINGS

The drawings illustrate one embodiment presently contemplated for carrying out the invention.

In the drawings.

DETAILED DESCRIPTION OF THE PREFERRED EMBODIMENT

In the following description of the invention, reference will be made to diagnostic imaging systems generally, and to specific diagnostic imaging modalities as examples. It is to be understood that the features and advantages of the present invention apply to many types of diagnostic imaging modalities, and that even when a feature is discussed with respect to a specific modality, the same feature or a corresponding feature is equally applicable in other imaging modalities as well.

Figure 1:
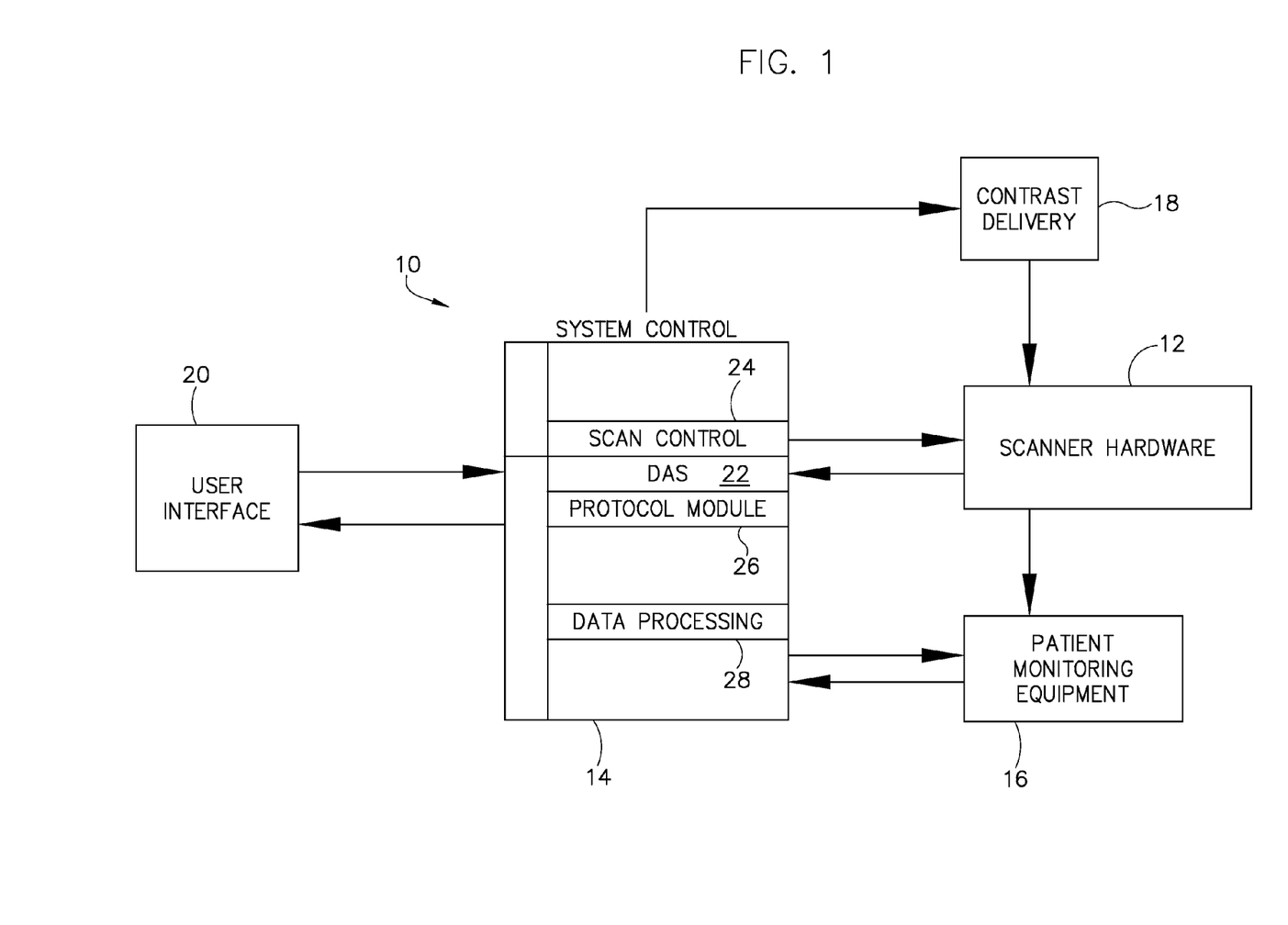
FIG. 1 is a block diagram of a diagnostic imaging system in accordance with an embodiment of the present invention.

Referring to FIG. 1, a block diagram of a diagnostic imaging system 10 is shown. Diagnostic imaging system 10 includes scanner hardware 12, controlled by a system control 14 to acquire images of a scan subject. System control 14 therefore includes a scanner control module 24 which operates to provide scanner hardware 12 with scan details, such as scan locations, scan durations, x-ray intensities, RF pulse sequences, ultrasound intensities, and the like. System control 14 also contains a data acquisition module 22 to receive scan data resulting from a scan, and a data processing module 28 to process the scan data for future scan localization, image reconstruction, etc.

One or more peripheral devices 16 may be used to monitor the scan subject and provide data to the system control 14. Monitoring equipment 16 may include ECG probes, an oximeter, a blood pressure monitor, and other similar devices. System control 14 may also control a contrast delivery device 18. In some embodiments, contrast delivery device 18 may be a contrast pump to control the delivery of a contrast agent to a scan subject intravenously. In other embodiments, contrast delivery device 18 may simply be an indicator which informs personnel when to inject a contrast agent or bolus, or when to orally administer the contrast agent or bolus. Such indication may also be shown on a user interface 20 of system control 14.

Interface 20 is used to allow operators to enter scan subject or patient information, select scan parameters, control contrast agent administration, and control scout, bolus, and image scans. As will be described below, static scan subject information and scan parameters entered on user interface 20, in combination with dynamic data from scan subject monitoring equipment 16, are used by a protocol module 26 of system control 14 to determine a scan/injection protocol which coordinates image data acquisition with peak contrast enhancement time.

Figure 2:
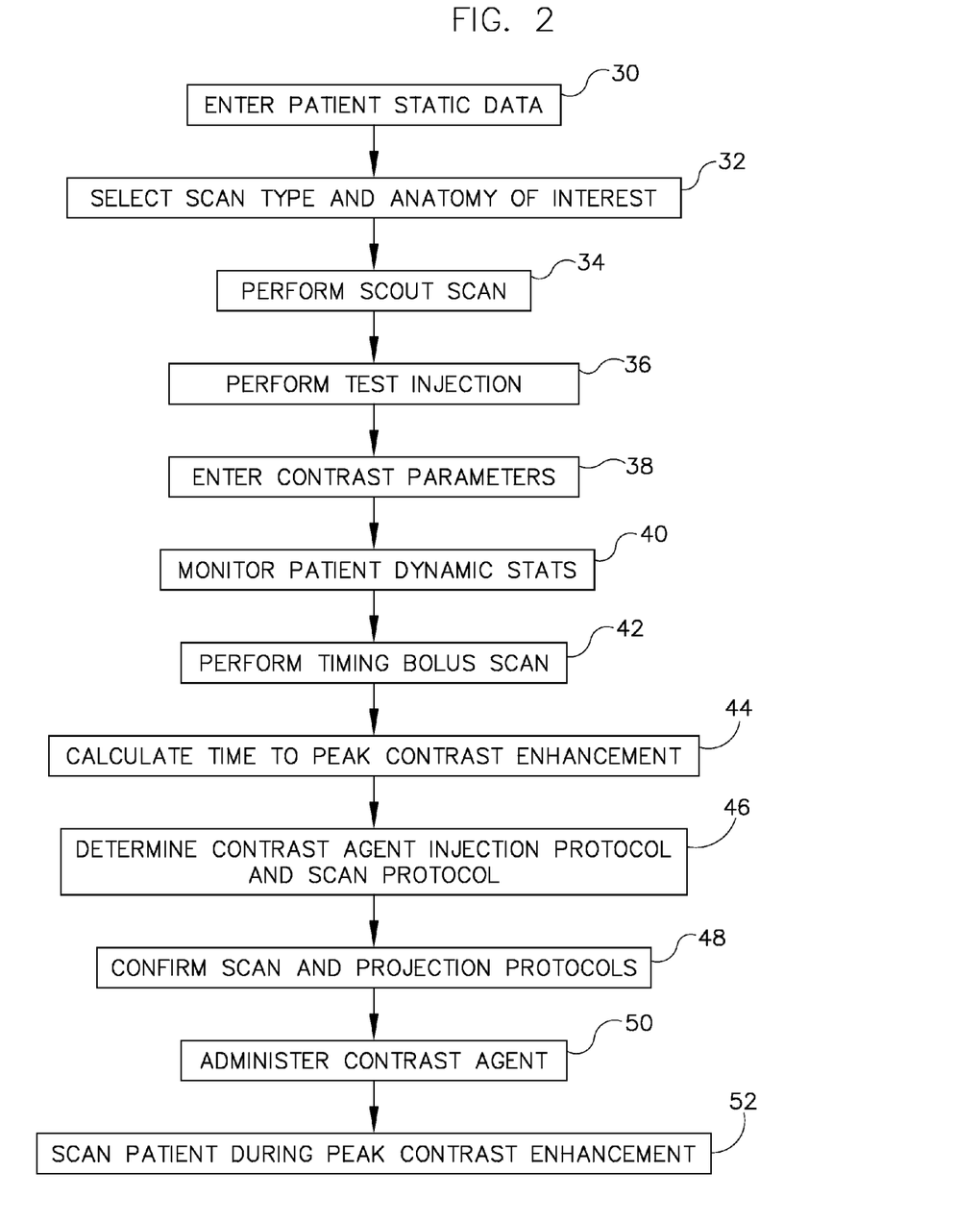
FIG. 2 is a flow chart setting forth one technique for controlling the diagnostic imaging system of FIG. 1.

Referring to FIG. 2, a flow chart is shown to illustrate a technique for controlling a contrast-enhanced diagnostic imaging scan in accordance with one embodiment of the present invention. The technique begins at block 30 with the entry of static data for a new scan subject. This data may include such parameters as subject age, gender, weight, height, and the like. The system may calculate a body mass index (BMI) value from these parameters, or the operator may enter a BMI value. Next, a scan type is selected and an anatomy of interest identified at block 32. For example, an operator may specify on a CT workstation that the scan to be performed is a routine helical scan to image the subject's spine or a CT angiography scan to image a subject's carotid artery. As another example, an operator could specify on an MR workstation that the scan to be performed is a diffusion weighted imaging (DWI) scan to be performed on the subject's aortic arteries.

Once the type of scan and anatomy of interest are entered, a scout scan may be performed at block 34 to provide localizing data for a subsequent imaging scan. Similarly, a test injection may be performed at block 36 to ensure correct needle placement and prevent extravasation. The maximum pressure during injection may also be recorded.

In addition to the scan subject and scan data discussed above, contrast injection-related parameters may also be entered at block 38. Such parameters may include the type, concentration, and volume of the contrast agent to be used, the type, concentration, and volume of the timing or tracking bolus to be used, the administration route (oral, intravenous), the administration method (automatic or manual), the needle type and gauge, and the presence or absence of an extravasation patch. Alternatively, the contrast injection-related parameters may be entered before or during the scout scan and test injection.

The system can begin monitoring scan subject dynamic parameters at block 40. These parameters may include heart rate, blood pressure, respiratory rate or average respiratory cycle, ECG signals, and other stats acquired by peripheral equipment monitoring the subject. The dynamic parameters may be monitored throughout the technique, or the system may begin monitoring dynamic parameters just prior to protocol calculations.

In some embodiments, a timing bolus scan is performed at block 42 to generate a time density curve. That is, the timing bolus scan records the perfusion of the bolus through the region of interest from the time of injection. From the density and location measurements of the time density curve, a time stamp may be marked corresponding to the projected peak contrast enhancement time of a contrast agent administered in a like manner. For example, in CT imaging, the time density curve may be a plot of contrast enhancement values in Hounsfield units over time.

After data has been entered by the user and acquired from the timing bolus scan, the system may calculate a peak contrast enhancement time for the actual administration of the contrast agent at block 44. By taking into account the static and dynamic scan subject parameters, the injection parameters, the scan parameters, and/or the timing bolus scan data, the system is able to accurately predict a post-injection time at which the contrast agent will provide maximum contrast enhancement. Knowing the duration of the scan, the system can provide a time delay before commencement of the scan such that the scan coincides with a period of maximum contrast enhancement.

At block 46, the system prescribes to an operator a scan and injection protocol to follow. Thus, an operator is informed of the timing between start of the contrast injection and start of image acquisition. An operator may be given the opportunity to confirm the protocols at block 48 or alter parameters to create a different protocol. Once the protocols have been confirmed, the operator can administer the contrast agent at block 50 (manually or automatically) and, after the time delay prescribed in the scan protocol, commence the scan at block 52.

Alternatively, embodiments of the invention may automate several of these steps. For example, the timing bolus scan may be replaced by administering a bolus in conjunction with the contrast agent and triggering the scan to commence in real-time based upon the bolus perfusion. Thus, the confirmation step and many of the calculations can be performed on the fly. In addition, the dynamic data provided by the scan subject monitoring equipment can be used to automatically adjust the timing of the scan. For example, if a patient's heart rate or blood pressure increase, the perfusion of the contrast agent may be quickened. The system can account for such variables in real time and hasten the commencement of the scan.

In further embodiments, the system control can also automatically adapt the scan parameters and contrast injection parameters based upon acquired image data, in combination with or as an alternative to adaptations based upon dynamic scan subject data. When a contrast agent is administered and a scan is commenced, image data will be acquired from the ROI. Based upon the image data acquired in real-time, the system can determine the present enhancement value of the contrast agent in the ROI and update or adapt such parameters as the flow rate or pressure of the injection process, x-ray tube current or voltage, x-ray dosage, pitch, gantry rotation, scan resolution, image data weighting, image acquisition trajectories, and the like, in real-time. Accordingly, if image data reveals that contrast enhancement has reached or will reach its peak enhancement value sooner or later than expected, the system can adjust scan and contrast parameters on the fly so that the image data acquisition, or a particular portion thereof, will still coincide with the time of maximum contrast enhancement. For example, in a CT scan, the system control could adjust the tube current and/or tube voltage in real time to scan a patient at a maximum dosage during the peak contrast enhancement, based upon enhancement calculations from acquired image data.

Figure 3:
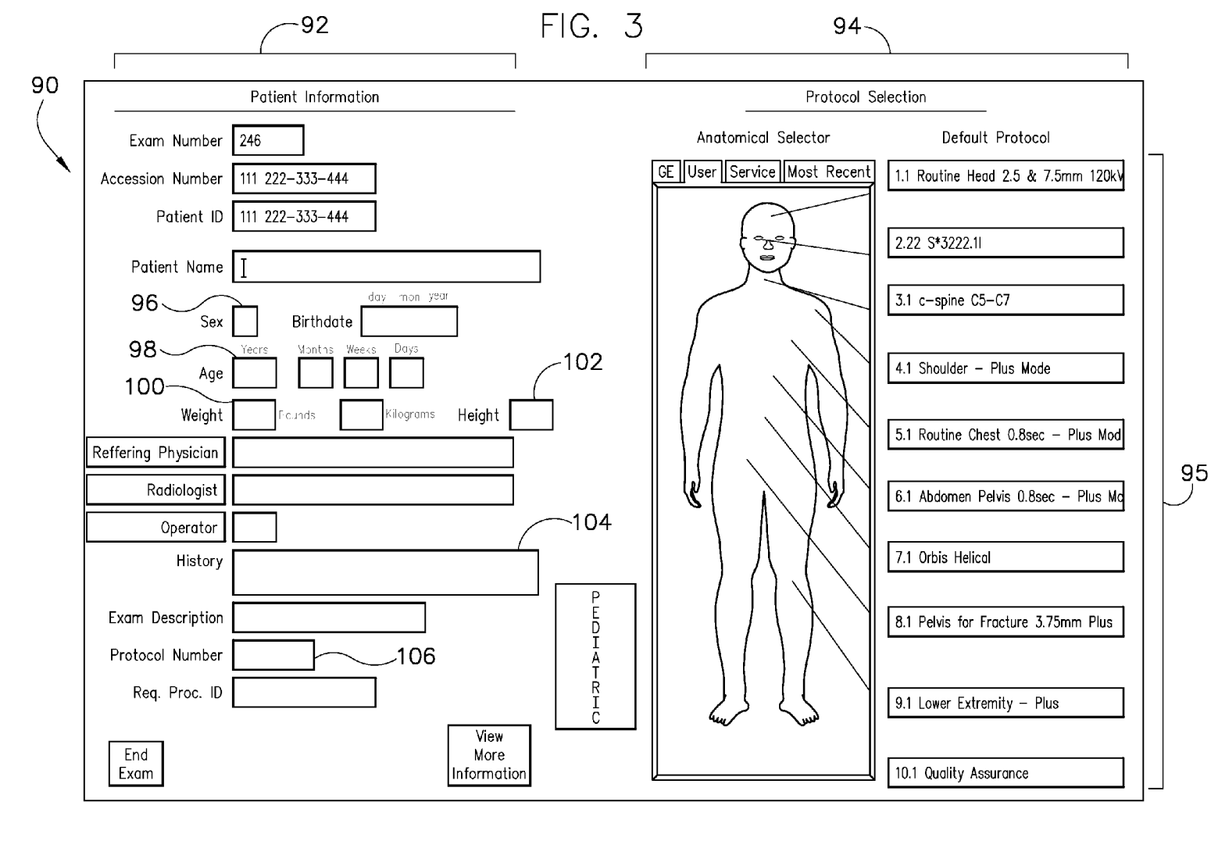
FIG. 3 is an exemplary start page for a user interface adapted to carry out the technique of FIG. 2.
Figure 4:
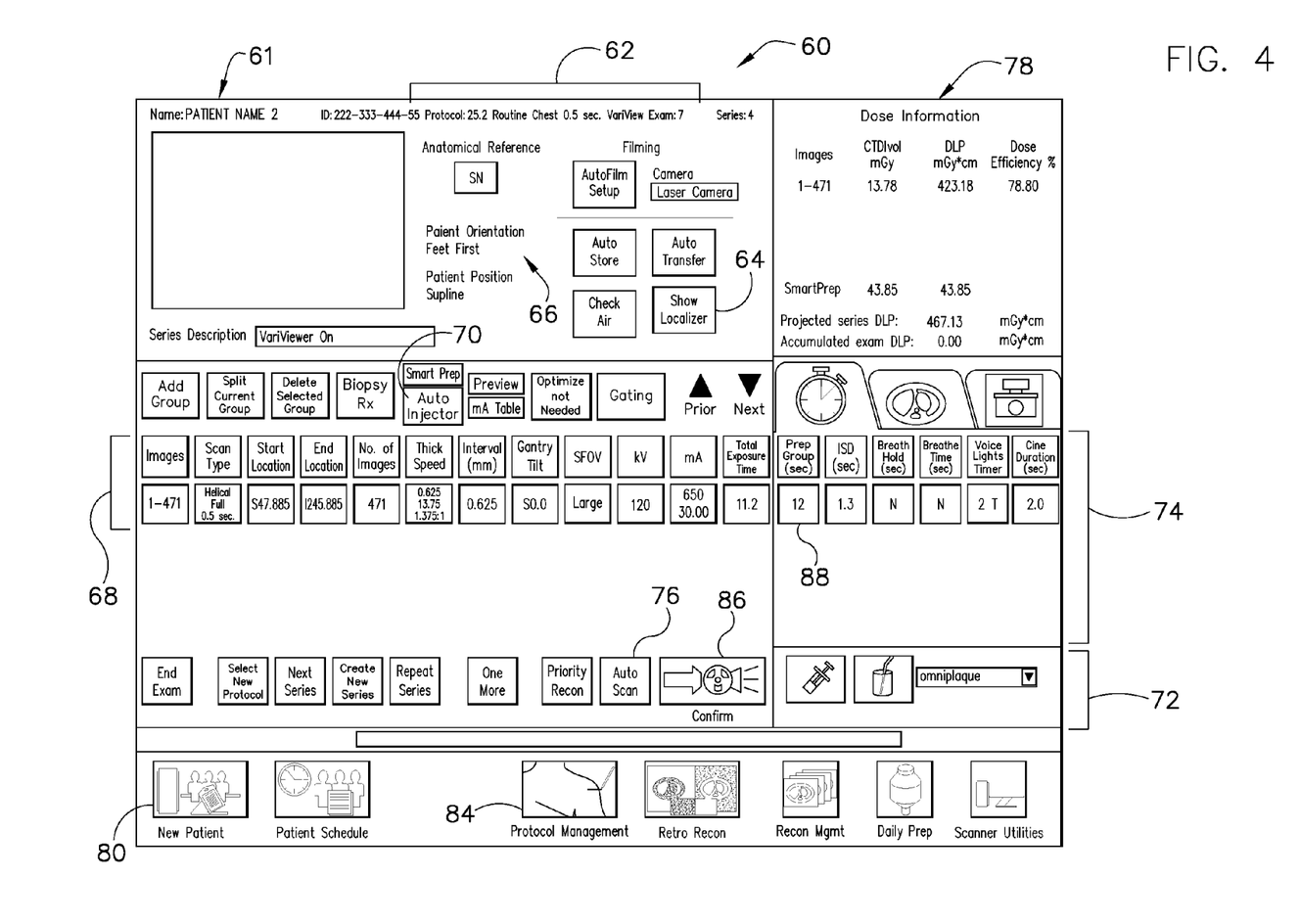
FIG. 4 is an exemplary main page for a user interface adapted to carry out the technique of FIG. 2.
Figure 5:
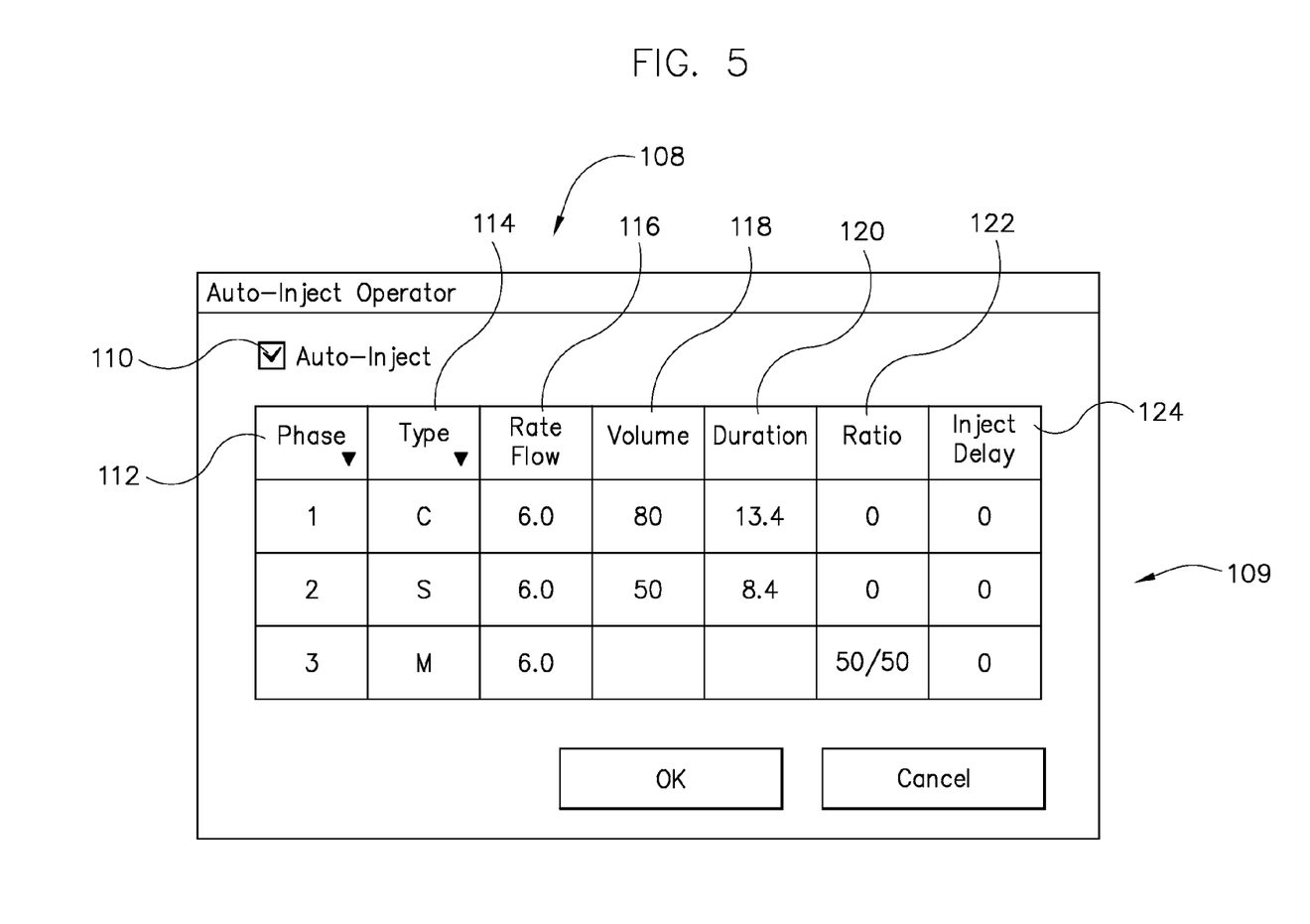
FIG. 5 is an optimization window for the main user interface page of FIG. 4.

Referring now to FIGS. 3-5, an exemplary user interface for carrying out embodiments of the invention is depicted. FIGS. 3-5 illustrate an embodiment of the invention relating to a CT imaging modality. However, as set forth above, the features and advantages described with respect to FIGS. 3-5 are equally and correspondingly applicable to other diagnostic imaging modalities.

FIG. 3 depicts an initial or start page 90 of the interface for entering new scan subject information 92 and selecting a scan type 94. In some embodiments, start page 90 is the first page displayed to an operator. Static scan subject parameters are entered into start page 90, including a scan subject's gender 96, age 98, weight 100, and height 104. Other relevant medical history data may be entered in box 104. An operator may give the impending scan a protocol number 106, to save the settings and data for later use. Alternatively, protocol number box 106 may be used to recall the settings and data of a previous scan. Start page 90 also allows a user to select the scan type and anatomy of interest 94 for the impending scan. As shown, a list of options is displayed for a user to click 95. In other embodiments, a user may separately select a scan type and an anatomy of interest from drop down menus, or may manually enter the type of scan and anatomy of interest.

FIG. 4 shows a main scanner control page 60, which may be displayed on a scanner or on a workstation associated with a scanner. Since scan and injection protocols of the present invention are individualized by scan subject, the interface displays the name of the patient 61 who is about to be scanned. When a new protocol is to be developed for a new patient, the "New Patient" button is clicked to re-set the interface. As depicted, a scan type 62 has already been selected for the current patient—a "Routine Chest 0.5 sec VariView Exam." A scout scan or "localizer" scan has also been acquired already, and may be displayed on a separate page or pop-up window (not shown) upon selection of the "Show Localizer" button. Position information of the patient is summarized in a nearby portion 66 of the interface.

Scan information is displayed in another scan section 68 of the interface. The scan information displayed in scan section 68 may be auto-populated upon selection of a scan type 62, though a user may also manually edit the settings in scan section 68. Similarly, a scan and injection protocol section 74 shows a variety of factors influencing the timing of the injection and subsequent scan, including the scan delay time 88. As shown, the delay time 88 calculated for the present scan is 12 s. The interface also allows a user to select whether the contrast agent will be manually or automatically administered in contrast delivery section 72. When a user alters the selected form of delivery 72, the interface may automatically re-calculate a scan delay time 88 if necessary. In the alternative, a user may simply select an auto-scan feature 76, in which case the scan sequence will automatically commence according to a real-time bolus tracking, as set forth above. Injection-related parameters are summarized in the injection data section 78 of the interface. The injection-related parameters 78, as well as the protocol data 74 (including the scan delay time 88) are automatically updated in response to significant changes in the dynamic scan subject parameters from the monitoring equipment, as described above.

An "Auto-Injector" button 70 causes the system to prescribe the injection protocol for the current scan subject. In accordance with the technique set forth above, static and dynamic patient-specific parameters are combined with injection parameters and scan parameters to coordinate the timing of the injection and the commencement of the scan into a particular protocol to efficiently utilize the contrast enhancement of the contrast agent administered to the scan subject. This may also include automatic adapting of the scan and injection parameters in real time to ensure image acquisition of a ROI coincides with a desired (or maximum) contrast enhancement in the ROI. A user may confirm the resulting protocol by clicking button 86 or may manually edit the resulting protocol or the settings according to which the system determines protocols by clicking button 84.

When the "Auto-Injector" button 70 is selected, the pop-up window of FIG. 5 is shown. Auto Inject Optimizer window 109 shows a number of details relating to the contrast injection. In certain embodiments, some or all of the details of window 109 may be pre-populated based upon the data already entered into control interface 60 (FIG. 4), such as scan type, contrast delivery type, scan delay, etc. Regardless, an operator is given the opportunity via optimizer window 109 to edit injection parameters such as the number of phases of contrast injection 112, the type of contrast agent 114 for each phase, the desired average rate of flow 116 for each contrast agent, the volume 118 to be used for each phase, the duration 120 of each phase, the saline ratio 122 of each administration, and the length of an injection delay 124, if used. Once an operator is satisfied with the parameters of the Auto Inject Optimizer window, the parameters will be summarized in the injection data section 78 of the system control interface 60 of FIG. 4. Alternatively, if a user has checked the auto-inject box 110 of FIG. 5, the parameters will be sent directly from an injector or contrast pump for automated delivery to the scan subject.

Accordingly, a system and method have been disclosed for determining individualized and improved contrast-enhanced imaging protocols. By taking into account a variety of factors influencing contrast delivery which are individual to each scan subject, the timing of the scan sequence can be made to more efficiently utilize the contrast enhancement of the contrast agent.

In particular, one embodiment of the invention includes a system control for a diagnostic imaging apparatus. The system control has a user interface adapted to permit a user to enter data specific to a given scan and a scan subject monitor configured to monitor at least one dynamic scan subject parameter. A scan protocol module of the system control is connected to receive data entered by the user on the user interface and the at least one dynamic scan subject parameter and is programmed to prescribe a scan protocol to optimize contrast enhancement. A contrast delivery device is controlled by the scan protocol module to cause a contrast agent to be delivered to a scan subject in accordance with the prescribed scan protocol. The system control also includes an acquisition control configured to coordinate commencement of the given scan in accordance with the scan protocol.

Another embodiment of the invention provides a method for contrast-enhanced diagnostic imaging. The method includes estimating, for a given scan subject, a post-delivery time for a desired contrast agent enhancement value, based on a number of subject parameters, a number of contrast agent parameters, and a number of scan parameters, and administering the contrast agent. At least a portion of an imaging scan sequence is then timed to coincide with the post-delivery desired contrast enhancement time of the contrast agent. The method further includes adapting at least one of the number of contrast agent parameters and the number of scan parameters during the scan sequence to maintain the timing of the desired contrast enhancement and the portion of the imaging scan sequence, and reconstructing an image of the scan subject based at least on scan data acquired during the post-delivery desired contrast enhancement time.

A further embodiment of the invention includes a computer readable storage medium which has a set of instructions stored thereon. The instructions, when executed by a computer, cause the computer to prompt a user to enter patient-specific information for a given scan patient and select a scan type. The computer is further caused to receive bolus tracking data for the given patient and provide an individualized scan protocol defining a contrast agent delivery and scan sequence timing, based upon the patient-specific information, the scan type, and the bolus tracking data.

The present invention has been described in terms of the preferred embodiment, and it is recognized that equivalents, alternatives, and modifications, aside from those expressly stated, are possible and within the scope of the appending claims.

What is claimed is:

1. A non-transitory computer-readable storage medium having a set of instructions stored thereon which, when executed by the computer, causes the computer to:
prompt a user to enter patient-specific information for a given scan patient;
prompt a user to select a scan type;
receive bolus tracking data for the given patient from a timing bolus scan;
identify an expected post-delivery peak contrast enhancement period based on the patient-specific information, the scan type, and the bolus tracking data;
provide an individualized scan protocol defining a contrast agent delivery, an x-ray dosage, and scan sequence timing, based upon the patient-specific information, the scan type, and the bolus tracking data;
perform a single dynamic scan session comprising a first scan sequence to acquire image data and a second scan sequence to acquire image data;
wherein, in performing the single dynamic scan session, the instructions further cause the computer to:
trigger commencement of the first scan sequence to acquire image data from a region-of-interest (ROI), the first scan sequence based on the individualized scan protocol;
reconstruct an image from the acquired image data;
update the x-ray dosage to an updated x-ray dosage based on the reconstructed image, the updated x-ray dosage comprising a maximum x-ray dosage to be applied during the single dynamic scan session and coincides with a post-delivery peak contrast enhancement period; and
trigger commencement of the second scan sequence to acquire image data from the ROI, the second scan sequence based on the updated x-ray dosage;
wherein, in updating the x-ray dosage to an updated x-ray dosage, the instructions further cause the computer to:
determine a present enhancement value of a contrast agent based on the reconstructed image;
determine if the present enhancement value of the contrast agent has reached or will reach the expected post-delivery peak contrast enhancement period sooner or later than expected;
if the present enhancement value of the contrast agent has reached or will reach the expected post-delivery peak contrast enhancement period sooner or later than expected, then adjust the x-ray dosage to the updated x-ray dosage; and
if the present enhancement value of the contrast agent has reached the expected post-delivery peak contrast enhancement period at an expected time, then the updated x-ray dosage is the same as the x-ray dosage.

2. The computer-readable storage medium of claim 1 wherein the set of instructions further causes the computer to receive the bolus tracking data as the bolus travels through the given patient.

3. The computer-readable storage medium of claim 2 wherein the set of instructions further causes the computer to trigger commencement of the first scan sequence based upon the bolus tracking data.

4. The computer-readable storage medium of claim 1 wherein the set of instructions further causes the computer to display default contrast agent parameters to a user after entry of the patient-specific information, selection of the scan type, and receipt of the bolus tracking data.

5. The computer-readable storage medium of claim 4 wherein the default contrast agent parameters include the projected post-delivery peak contrast enhancement time.

6. The computer-readable storage medium of claim 4 wherein the instructions further cause the computer to display the contrast agent parameters and a number of scan parameters to the user and prompt the user to confirm the parameters prior to contrast delivery and scan commencement.

7. The computer-readable storage medium of claim 1 wherein the instructions further cause the computer to control a contrast pump to deliver a contrast agent to the patient in accordance with the protocol.

8. The computer readable storage medium of claim 1 wherein, if the present enhancement of contrast has reached or will reach the expected post-delivery peak contrast enhancement period sooner or later than expected, the instructions further cause the computer to adjust at least one of scan parameters and contrast agent parameters in the second scan sequence.

9. The computer readable storage medium of claim 8 wherein, in adjusting at least one of the scan parameters and the contrast agent parameters, the instructions further cause the computer to adjust pitch, or gantry rotation in a CT scan such that a period of maximum x-ray dosage of the CT scan substantially coincides with a peak contrast enhancement value.

10. The computer readable storage medium of claim 8 wherein, in adjusting at least one of the scan parameters and the contrast agent parameters, the instructions further cause the computer to adjust contrast agent flow rate, pressure, or volume to achieve a maximum contrast enhancement value during a period of maximum x-ray dosage of a CT scan.

11. A system control for a diagnostic imaging apparatus comprising:
a user interface adapted to permit a user to enter data specific to a given scan;
a contrast delivery device configured to cause a contrast agent to be delivered to a scan subject;
a data processing module configured to reconstruct an image from scan data; and
a scan protocol module connected to receive data entered by the user on the user interface and programmed to:
identify an expected post-delivery peak contrast enhancement period based on entered data specific to the given scan;
prescribe a scan protocol for a first image acquisition of the given scan to acquire scan data from a region-of-interest (ROI);
reconstruct an image from scan data acquired from the first image acquisition;
determine an enhancement value of the contrast agent in the ROI from the reconstructed image;
determine if the enhancement value of the contrast agent has reached or will reach the expected post-delivery peak contrast enhancement period sooner or later than expected;
if the enhancement value of the contrast agent has not or will not reach the expected post-delivery peak contrast enhancement period sooner or later than expected, then:
adjust an x-ray dosage of the scan protocol the adjusted x-ray dosage comprising a maximum x-ray dosage to be applied during the given scan and coincides with a post-delivery peak contrast enhancement period; and
cause the commencement of a second image acquisition of the given scan to acquire scan data from the ROI, the second image acquisition performed using the adjusted x-ray dosage; and
if the enhancement value of the contrast agent has reached or will reach the expected post-delivery peak contrast enhancement period at the expected peak contrast enhancement period, then do not adjust the x-ray dosage of the scan protocol.

12. The system control of claim 11 wherein the data specific to the given scan includes at least one of a static scan subject parameter and a scan type.

13. The system control of claim 11 wherein the prescribed scan protocol includes a contrast agent delivery protocol.

14. The system control of claim 13 wherein the prescribed scan protocol includes a number of contrast agent delivery protocols corresponding to a number of injection phases of a diagnostic imaging scan.

15. The system control of claim 11 wherein the contrast delivery device includes at least one of an automated contrast injection device to inject the contrast agent and an indicator to inform an operator when to administer the contrast agent.

16. A method for contrast-enhanced diagnostic imaging comprising:
estimating, for a given scan subject, a post-delivery peak contrast agent enhancement period based on a number of subject parameters, a number of contrast agent parameters, and a number of scan parameters of an imaging scan sequence, the imaging scan sequence comprising a single dynamic scan session;
executing the imaging scan sequence comprising a data scan portion timed to coincide with the estimated post-delivery peak contrast agent enhancement period;
controlling administration of a contrast agent via a scan protocol module of a diagnostic imaging system during the imaging scan sequence;
acquiring scan data of a region-of-interest (ROI) of the scan subject during the data scan portion;
reconstructing an image of the ROI of the scan subject based at least on the acquired scan data;
comparing a present enhancement value of the contrast agent with the estimated post-delivery peak contrast agent enhancement period based on the reconstructed image;
if the present enhancement value of the contrast agent has reached or will reach the estimated peak contrast agent enhancement period sooner or later than expected, then:
adapting a first scan parameter of the number of scan parameters of the imaging scan sequence to adjust an x-ray dosage of the imaging scan sequence so as to generate an adapted imaging scan sequence, with the adjusted x-ray dosage to be applied so as to coincide with a post-delivery peak contrast enhancement period;
executing the adapted imaging scan sequence comprising the adapted first scan parameter; and
acquiring scan data of the ROI of the scan subject during the data scan portion of the adapted imaging scan sequence; and
if the present enhancement value of the contrast agent has reached or will reach the post-delivery peak contrast agent enhancement period at the estimated post-delivery peak contrast agent enhancement period, then do not adapt the scan parameters of the imaging scan sequence.

17. The method of claim 16 wherein adapting a first scan parameter to adjust an x-ray dosage of the imaging scan sequence comprises causing a maximum x-ray dosage to be applied during a peak contrast enhancement period of the contrast agent.

18. The method of claim 17 wherein the number of subject parameters include at least one of subject weight, gender, age, height, and body mass index, heart rate, blood pressure, respiratory rate, and timing bolus data.

19. The method of claim 16 wherein the number of contrast agent parameters include at least one of contrast agent type, bolus type, number of injection phases, contrast agent volume, contrast agent flow rate, injection duration, and contrast enhancement duration.

* * * * *